United States Patent
Theuerkauf et al.

(10) Patent No.: US 9,517,991 B2
(45) Date of Patent: Dec. 13, 2016

(54) METHOD FOR PRODUCING 2-METHYLBUTANAL FROM THE SECONDARY FLOWS ARISING IN THE PRODUCTION OF MIXTURES OF ISOMERIC ALPHA, BETA-UNSATURATED DECENALS

(71) Applicant: Oxea GmbH, Oberhausen (DE)

(72) Inventors: Jens Theuerkauf, Krefeld (DE); Heinz Strutz, Moers (DE)

(73) Assignee: OXEA GMBH, Oberhausen (DE)

( * ) Notice: Subject to any disclaimer, the term of this patent is extended or adjusted under 35 U.S.C. 154(b) by 0 days.

(21) Appl. No.: 15/033,661

(22) PCT Filed: Nov. 14, 2014

(86) PCT No.: PCT/EP2014/003057
§ 371 (c)(1),
(2) Date: May 2, 2016

(87) PCT Pub. No.: WO2015/082044
PCT Pub. Date: Jun. 11, 2015

(65) Prior Publication Data
US 2016/0304430 A1    Oct. 20, 2016

(30) Foreign Application Priority Data
Dec. 5, 2013 (DE) .......... 10 2013 020 322

(51) Int. Cl.
C07C 45/50 (2006.01)
C07C 45/62 (2006.01)
C07C 29/00 (2006.01)
C07C 45/82 (2006.01)
C07C 45/74 (2006.01)
C07C 29/17 (2006.01)

(52) U.S. Cl.
CPC ............ C07C 45/82 (2013.01); C07C 29/175 (2013.01); C07C 45/50 (2013.01); C07C 45/62 (2013.01); C07C 45/74 (2013.01)

(58) Field of Classification Search
CPC ......... C07C 45/50; C07C 45/62; C07C 29/175
USPC ........................................ 568/451
See application file for complete search history.

(56) References Cited

U.S. PATENT DOCUMENTS

| | | |
|---|---|---|
| 4,426,542 A | 1/1984 | Barker et al. |
| 4,599,206 A | 7/1986 | Billig et al. |
| 4,710,316 A | 12/1987 | Hafner et al. |
| 4,950,800 A | 8/1990 | Weber et al. |
| 5,369,162 A | 11/1994 | Bahrmann et al. |
| 5,463,147 A | 10/1995 | Bahrmann et al. |
| 6,340,778 B1 | 1/2002 | Bueschken et al. |
| 6,680,395 B2 | 1/2004 | Springer |
| 8,461,394 B2 | 6/2013 | Lueken et al. |
| 8,907,129 B2 | 12/2014 | Grass et al. |
| 9,266,808 B2 | 2/2016 | Sigl et al. |

FOREIGN PATENT DOCUMENTS

| | | |
|---|---|---|
| DE | 2155672 A1 | 6/1972 |
| DE | 3744212 A1 | 7/1989 |
| DE | 4210026 A1 | 9/1993 |
| DE | 4333324 A1 | 4/1995 |
| DE | 19957522 A1 | 5/2001 |
| DE | 10010770 C1 | 9/2001 |
| DE | 10108474 A1 | 9/2002 |
| DE | 10108475 A1 | 9/2002 |
| DE | 10225282 A1 | 12/2003 |
| DE | 102008002187 A1 | 12/2009 |
| DE | 102009027978 A1 | 1/2011 |
| EP | 0213639 A2 | 3/1987 |
| EP | 0217159 A2 | 4/1987 |
| EP | 0366089 A2 | 5/1990 |
| GB | 1336037 | 11/1973 |
| WO | 2005028407 A1 | 3/2005 |
| WO | 2008065171 A1 | 6/2008 |
| WO | 2010117391 A1 | 10/2010 |

OTHER PUBLICATIONS

International Preliminary Report on Patentability dated Jun. 9, 2016.

*Primary Examiner* — Sikarl Witherspoon
(74) *Attorney, Agent, or Firm* — Michael W. Ferrell

(57) ABSTRACT

A process for preparing 2-methylbutanal from the secondary streams obtained in the preparation of mixtures of isomeric α,β-unsaturated decenals, characterized in that a) a mixture comprising linear butenes is reacted in the presence of transition metal compounds of group VIII of the Periodic Table of the Elements with carbon monoxide and hydrogen at elevated temperature and elevated pressure to give a pentanal mixture; b) the pentanal mixture obtained in step a) is converted in the presence of basic compounds to a mixture of isomeric α,β-unsaturated decenals; and c) the mixture obtained in step b) is separated into a stream enriched with unconverted 2-methylbutanal and a stream enriched with a mixture of isomeric α,β-unsaturated decenals; with the proviso that the stream which has been separated off in step c) and is enriched with unconverted 2-methylbutanal is reacted with formaldehyde.

20 Claims, No Drawings

METHOD FOR PRODUCING 2-METHYLBUTANAL FROM THE SECONDARY FLOWS ARISING IN THE PRODUCTION OF MIXTURES OF ISOMERIC ALPHA, BETA-UNSATURATED DECENALS

CLAIM FOR PRIORITY

This application is a national phase application of PCT/EP2014/003057 FILED Nov. 14, 2014 which was based on application DE 10 2013 020 322.8 FILED Dec. 5, 2013. The priorities of PCT/EP2014/003057 and DE 10 2013 020 322.8 are hereby claimed and their disclosures incorporated herein by reference.

BACKGROUND

The present invention relates to a process for preparing 2-methylbutanal from secondary streams obtained in the preparation of mixtures of isomeric α,β-unsaturated decenals. Pentanals, also called valeraldehydes, have gained economic significance as intermediates in industrial organic chemistry. They occur in four different structural isomers as linear n-pentanal, branched 2-methylbutanal, branched 3-methylbutanal and highly branched 2,2-dimethylpropanal or pivalaldehyde. Pentanals can be used as such, for example for the production of fragrances, or in the form of the derivatization products thereof, such as pentanols, pentanoic acids or pentylamines. The pentanals can be processed in pure isomeric form or in the form of an isomer mixture (Weissermel, Arpe, Industrielle Organische Chemie [Industrial Organic Chemistry], 3rd edition, VCH Verlagsgesellschaft mbH, Weinheim, 1988, page 218; Schneidmeir, Chemiker-Zeitung, volume 96 (1972), no. 7, pages 383-387).

Because of the reactive aldehyde group, pentanals in a basic medium can enter into an aldol addition reaction to give pentanal dimerization products having ten carbon atoms. If at least one of the pentanal isomers has two reactive hydrogen atoms in the α position to the carbonyl group, the aldol addition product formed at first can be converted to the α,β-unsaturated aldol condensation product or α,β-unsaturated decenal with elimination of water. The formation of the double bond in the α,β position relative to the carbonyl carbon atom with elimination of water is frequently also referred to as crotonization.

In the aldol condensation of pentanals, either structurally identical pentanals can react in a self-condensation or structurally different pentanals in a co-condensation. Among the pentanals, linear n-pentanal has the greatest reactivity, and the aldol condensation of n-pentanal-containing pentanal mixtures preferentially affords 2-propylheptenal from the self-condensation of n-pentanal. The aldol addition reaction and aldol condensation reaction of pentanals is typically conducted in the presence of basic catalysts such as aqueous alkali metal hydroxide solutions.

The aldol condensation reaction of pentanals to give mixtures of isomeric α,β-unsaturated decenals can be conducted, for example, in a tubular reactor as described in DE 10 2009 001594 A1 and DE 199 57 522 A1, in a stirred tank as known from EP 0 366 089 A2, or in a reaction mixing pump according to DE 10 2009 045 139 A1. According to the proportions of the isomeric pentanals in the feed mixture, mixtures comprising structurally different α,β-unsaturated decenals are obtained.

U.S. Pat. No. 4,426,542 A likewise concerns the aldolization of a pentanal mixture in the presence of an aqueous alkali metal hydroxide solution and subsequent hydrogenation to give a mixture of isomeric decanols. Unreacted aldehydes can be removed by distillation from the decenal mixture prior to the hydrogenation stage. The isomeric pentanals are obtainable by hydroformylation reaction of linear butenes.

The resultant mixtures of isomeric α,β-unsaturated decenals likewise have increasing economic significance as organic intermediates. The complete hydrogenation of the olefinic double bond and the aldehyde group affords a mixture of structurally isomeric decanols which are processed further by esterification with aromatic di- or polycarboxylic acids and aliphatic dicarboxylic acids to give plasticizers for thermoplastics. The dependence of the plasticizer properties on the composition of the decanol mixture is examined, for example, in EP 0 366 089 A2. The use of isomeric decanol mixtures as plasticizer alcohols which are obtained by complete hydrogenation of mixtures of isomeric α,β-unsaturated decenals is likewise described in DE 42 100 26 A1 and DE 43 33 324 A1.

α,β-Unsaturated decenals can likewise be hydrogenated selectively to give a mixture of isomeric decanals which, because of their aldehyde reactivity, can be converted to further conversion products, especially to carboxylic acids by oxidation (DE 10 2009 027 978 A1). Isomeric decanoic acids find use for production of lubricant esters or serve for preparation of peracids for polymerization reactions.

Pentanals are prepared industrially by reaction of butenes with synthesis gas, a mixture of carbon monoxide and hydrogen, in the presence of transition metal compounds. The reaction of olefins with synthesis gas is also referred to as the hydroformylation reaction or oxo reaction, and the hydroformylation of but-1-ene affords, as well as the straight-chain n-aldehyde n-pentanal, also certain proportions of the isoaldehyde 2-methylbutanal (Ullmann's Encyclopedia of Industrial Chemistry, 6th edition, 2003, Wiley-VCH Verlag GmbH & Co. KGaA, Weinheim, vol. 2, pages 73-74; vol. 25, pages 286-289).

Butenes are obtained industrially by the steamcracking of naphtha. Since the linear butenes but-1-ene and but-2-ene are of significance for the preparation of mixtures of isomeric α,β-unsaturated decenals, it is customary to first separate 1,3-butadiene from the butene cut from the naphtha cracking to form raffinate I, and then to remove isobutene to form raffinate II (Weissermel, Arpe, Industrielle Organische Chemie, 3rd edition, VCH Verlagsgesellschaft mbH, 1988, pages 71-79). For the subsequent hydroformylation reaction, predominantly raffinate II is used, in which a small residual isobutene content can be permitted. In special cases, it is also possible to process raffinate I having a high isobutene content, and occasionally also a but-1-ene-depleted raffinate II, which can also be referred to as raffinate III.

The hydroformylation reaction can be conducted either in the presence or in the absence of complex-forming compounds, for example in the presence of organophosphorus compounds. According to EP 0 366 089 A2, a homogeneous organic solution is employed with rhodium triphenylphosphine catalysis. Since the aim is generally a maximum proportion of n-pentanal compared to 2-methylbutanal in the pentanal mixture formed, the hydroformylation reaction is frequently conducted in the presence of homogeneously dissolved transition metal complexes, which first enable isomerization of the but-2-ene to but-1-ene, which is then hydroformylated predominantly to n-pentanal. Rhodium complex catalysts suitable for the isomerizing hydroformylation of a mixture of linear butenes are described, for example, in DE 102 25 282 A1, in which the complex ligands have a xanthene skeleton.

Rhodium complex catalysts based on bisphosphite ligands together with sterically hindered secondary amines, which are likewise suitable for the isomerizing hydroformylation of a mixture of linear butenes, are discussed in DE 10 2008 002 187 A1. Two-stage process variants are also known, for example according to DE 43 33 324 A1, DE 42 10 026 A1, DE 101 08 474 A1 and DE 101 08 475. In the first stage, but-1-ene is preferentially converted, while, in the second stage, the but-2-ene-containing offgas from the first stage is hydroformylated to give a mixture of n-pentanal and 2-methyl-butanal. According to DE 43 33 324 A1 and DE 101 08 474 A1, the first hydroformylation stage can also be conducted in the presence of water-soluble rhodium complex catalysts. In this type of reaction regime, a liquid aqueous catalyst solution is present alongside the liquid organic reaction solution, which, after leaving the hydroformylation zone, can be separated from one another in a simple manner by phase separation. Because of the presence of an aqueous phase and an organic liquid phase, this type of reaction regime is also referred to as a heterogeneous process or biphasic process.

Because of the increasing demand for mixtures of isomeric α,β-unsaturated decenals, the hydroformylation reaction of the butene feed mixture gives considerable amounts of 2-methyl-butanal and to a certain degree also 3-methylbutanal, even when the use of suitable catalysts which promote isomerizing hydroformylation results in preferential n-pentanal formation. There is therefore a need for a process in which the 2-methyl-butanal obtained in the preparation of mixtures of isomeric α,β-unsaturated decenals can be obtained in maximum quality and free of impurities, such that the 2-methylbutanal obtained can be used with maximum versatility and the overall process for production of mixtures of isomeric α,β-unsaturated decenals can thus be made more economically viable.

SUMMARY OF INVENTION

The present invention therefore consists in a process for preparing 2-methylbutanal from the secondary streams obtained in the preparation of mixtures of isomeric α,β-unsaturated decenals, characterized in that
a) a mixture comprising linear butenes is reacted in the presence of transition metal compounds of group VIII of the Periodic Table of the Elements with carbon monoxide and hydrogen at elevated temperature and elevated pressure to give a pentanal mixture;
b) the pentanal mixture obtained in step a) is converted in the presence of basic compounds to a mixture of isomeric α,β-unsaturated decenals; and
c) the mixture obtained in step b) is separated into a stream enriched with unconverted 2-methylbutanal and a stream enriched with a mixture of isomeric α,β-unsaturated decenals; with the proviso that the stream which has been separated off in step c) and is enriched with unconverted 2-methylbutanal is reacted with formaldehyde.

DETAILED DESCRIPTION

Feedstocks for the process of the invention are hydrocarbon mixtures typically containing very small amounts, if any, of polyunsaturated compounds and acetylene compounds and containing at least one of the olefins cis-but-2-ene, trans-but-2-ene and but-1-ene. In addition, the feed mixture may include varying proportions of isobutene. Feed mixtures of this kind are industrially available as raffinate I, raffinate II or raffinate III.

The butene hydroformylation can be conducted in a homogeneous variant in the organic reaction medium with dissolved transition metal catalysts of group VIII of the Periodic Table of the Elements in the unmodified variant, or in the variant modified with complex ligands. Particularly effective solvents in the organic reaction medium have been found to be the higher-boiling condensation compounds of the pentanals, especially the trimers, which are obtained as by-products in the hydroformylation, and mixtures thereof with the pentanals to be prepared, and so a further addition to the solution is not absolutely necessary. In some cases, however, an addition of solvent may be found to be appropriate. The solvents used are organic compounds in which starting material, reaction product and catalyst are soluble. Examples of such compounds are aromatic hydrocarbons such as benzene and toluene or the isomeric xylenes and mesitylene. Other commonly used solvents are paraffin oil, cyclohexane, n-hexane, n-heptane or n-octane, ethers such as tetrahydrofuran, ketones or Texanol® from Eastman. When the homogeneous variant in their presence is employed, suitable complexing ligands are triarylphosphines such as triphenylphosphine (EP 0 366 089 A2), diphosphines, for example those based on the xanthene skeleton (DE 102 25 282 A1), phosphites as described, for example, in U.S. Pat. No. 4,599,206, or diphosphites, for example described in EP 0 213 639 A2 and DE 10 2008 002 187 A1. It is also possible to use mixtures of complex ligands, for example of triarylphosphines with phosphites or diphosphites, as known from WO 2010/117391 A1, in the hydroformylation reaction.

Through the choice of the composition of the butene feed mixture and the hydroformylation conditions, it is possible to control the ratio of n-pentanal to 2-methylbutanal.

If the aim is a maximum proportion of n-pentanal compared to 2-methylbutanal in the hydroformylation mixture, it is advisable, as well as a but-1-ene-rich feed stream, to use modified transition metal catalysts which at first bring about isomerization of the residual but-2-ene content to but-1-ene, which is then hydroformylated predominantly to n-pentanal. In one configuration of the process of the invention, it is possible to use the hydroformylation catalysts that are known from DE 102 25 282 A1 and have complex ligands based on the xanthene skeleton, or the hydroformylation catalysts that are known from EP 0 213 639 A2 or DE 10 2008 002 187 A1 and are based on sterically hindered diphosphites.

High proportions of n-pentanal can also be obtained in a two-stage process variant which is known per se from DE 101 08 474 A1 and DE 101 08 475. In the first stage, which can likewise be conducted by the heterogeneous variant in the presence of water with water-soluble complex ligands, for example with sulfonated phosphines such as triphenylphosphine with different degrees of sulfonation, predominantly but-1-ene reacts in high selectivity to give n-pentanal, and the but-2-ene-enriched offgas is subsequently converted in a second stage under isomerizing conditions to a pentanal mixture having a high n-pentanal content. By combining the streams from the first and second hydroformylation stages, it is possible to prepare a pentanal mixture having a high proportion of n-pentanal relative to 2-methylbutanal.

If the aim is a high proportion of 2-methylbutanal in the pentanal mixture, for example because of market circumstances, or if this arises because of the composition of the butene feed mixture, preference is given to working in the absence of complex ligands in the unmodified mode of operation. In this case, the active hydroformylation catalyst forms from the transition metal or transition metal compound and carbon monoxide. It is assumed in the specialist literature that the transition metal compound $HM(CO)_4$ is the catalytically active transition metal species in the unmodified transition metal catalysis.

With increasing isobutene content in the butene feed mixture, the proportion of 3-methylbutanal in the hydroformylation product also increases.

In the modified variant, the molar ratio of transition metal to complex ligand is generally 1:1 to 1:1000, but it may also be higher. Preference is given to using the transition metal and the complex ligand in a molar ratio of 1:3 to 1:500, preferably 1:50 to 1:300. The modified hydroformylation reaction of the butene mixture is typically conducted at temperatures of 50 to 160° C. and pressures of 0.2 to 15 MPa. The transition metal concentration is generally 10 to 700 ppm, preferably 25 to 500 ppm, based on the reaction mixture.

If the unmodified variant is employed, the transition metal is used in smaller amounts, generally in an amount of 1 to 100 ppm, preferably 2 to 30 ppm, based on the amount of butene used. It is appropriate to work at higher pressures in the range from 5 to 70 MPa, preferably from 5 to 60 MPa and especially from 10 to 30 MPa. Suitable reaction temperatures vary within the range from 50 to 180° C., preferably from 50 to 150° C. and especially from 100 to 150° C.

The composition of the synthesis gas can be varied within wide limits. In general, mixtures in which the molar ratio of carbon monoxide to hydrogen is 5:1 to 1:5 are used. Typically, this ratio is 1:1 or deviates only slightly from this value in favor of hydrogen. The mixture comprising linear butenes can be supplied to the reaction zone as such or in solution with organic solvents, such as hydrocarbons.

The transition metals of group VIII of the Periodic Table of the Elements used are preferably cobalt, rhodium, iridium, nickel, palladium, platinum, iron or ruthenium, and especially rhodium and cobalt. The modified or unmodified transition metal catalyst forms under the conditions of the hydroformylation reaction from the transition metal compounds used, such as the salts thereof, such as chlorides, nitrates, sulfates, acetates, pentanoates or 2-ethylhexanoates, the chalcogenides thereof, such as oxides or sulfides, the carbonyl compounds thereof, such as $M_2(CO)_8$, $M_4(CO)_{12}$, $M_6(CO)_{16}$, $M_2(CO)_9$, $M_3(CO)_{12}$, the organo-transition metal compounds thereof, such as carbonyl acetylacetonates or cyclooctadienyl acetates or chlorides. It is possible here to use the transition metal compound in solid form or appropriately in solution. Particularly suitable transition metal compounds which are used as catalyst precursor are rhodium pentanoate, rhodium acetate, rhodium 2-ethylhexanoate or cobalt pentanoate, cobalt acetate or cobalt 2-ethylhexanoate or $Co_2(CO)_8$, $Co_4(CO)_{12}$, $R_2(CO)_8$, $Rh_4(CO)_{12}$ or $Rh_6(CO)_{16}$ or cyclopentadienylrhodium compounds, rhodium acetylacetonate or rhodium dicarbonyl acetylacetonate. Preference is given to using rhodium oxide and especially rhodium acetate, rhodium 2-ethylhexanoate and rhodium pentanoate.

Alternatively, it is also possible first to preform the transition metal catalyst in a pre-carbonylation stage and then to supply it to the actual hydroformylation stage. The preforming conditions generally correspond to the hydroformylation conditions.

The hydroformylation stage can be conducted either batchwise or continuously. The pentanal mixture formed is separated from the hydroformylation catalyst by conventional methods, for example by distillation in the homogeneous process regime or by simple phase separation from the aqueous catalyst solution in the heterogeneous or biphasic process regime.

The transition metal catalyst, optionally after addition of fresh transition metal compound and optionally fresh ligand if the modified mode of operation is being employed, and after removal of a portion of the aldehyde condensation products formed in the course of the reaction, is recycled into the reaction zone.

The requirement for a particular composition of the pentanal mixture obtained with regard to the n-pentanal, 2-methylbutanal and 3-methylbutanal isomers is guided by the market circumstances and can be controlled via the composition of the butene feed mixture and via the choice of the hydroformylation conditions. Frequently, the aim is a pentanal mixture containing generally at least 85 mol % of n-pentanal, less than 15 mol % of 2-methylbutanal and, depending on the isobutene content, less than 5 mol % of 3-methylbutanal, preferably less than 1 mol % and especially less than 0.2 mol % of 3-methylbutanal, based in each case on the sum total of pentanals. But pentanal mixtures having a higher proportion of 2-methylbutanal may also be demanded by the market. The pentanal mixture obtained after the hydroformylation stage and after catalyst removal, which can also be regarded as crude hydroformylation product, optionally after distillative workup, is then subjected to an aldol condensation to give the α,β-unsaturated decenals under the action of basic catalysts. Catalysts employed are alkali metal carbonates or alkali metal hydroxides, especially compounds of sodium or of potassium and amines, preferably tertiary amines, such as triethylamine, tri-n-propylamine, tri-n-butylamine, in each case as aqueous solutions. The concentration of the basic catalyst in the aqueous solution is typically 0.1% to 10% by weight, preferably 0.1% to 3% by weight. Operation is effected at temperatures of 20 to 160° C., especially 40 to 130° C., and at standard pressure or at up to about 1 MPa of elevated pressure. Suitable reaction vessels are stirred tanks or a stirred tank cascade, a flow tube or a mixing pump. The use of static mixers allows vigorous mixing of the aqueous catalyst phase with the organic aldehyde phase.

The reaction time is a few minutes to several hours and is dependent especially on the catalyst type and on the reaction temperature. n-Pentanal has the highest reaction rate, and the α,β-unsaturated self-condensation product 2-propylheptenal is formed as the main product. 2-Methylbutanal reacts with n-pentanal to give the co-condensation product 2-propyl-4-methylhexenal. If 3-methylbutanal is additionally still present, the 2-isopropyl-5-methylhexenal self-condensation product, and also the 2-propyl-5-methylhexenal and 2-isopropyl-heptenal co-condensation products with n-pentanal and the 2-isopropyl-4-methylhexenal co-condensation product with 2-methylbutanal are formed. Since 2-methylbutanal is less reactive compared to n-pentanal and 3-methylbutanal, after the aldol condensation reaction has ended, the crude mixture obtained, as well as the isomeric α,β-unsaturated decenals formed, will also contain proportions of unreacted 2-methylbutanal. The proportions of 2-methylbutanal in the reaction mixture can be controlled in the aldol condensation reaction by the reaction conditions, for example by choice of reaction temperature or by use of solvents having phase transfer properties, such as the oligomers of ethylene glycol or propylene glycol.

Subsequently, the mixture of the isomeric α,β-unsaturated decenals and unconverted starting materials is worked up by distillation. First of all, the volatile 2-methylbutanal and any 3-methylbutanal components and residual amounts of n-pentanal are drawn off as a secondary stream. Subsequently, separately therefrom, the mixture of isomeric α,β-unsaturated decenals is distilled off from higher aldol condensation products and high boilers. The distillation is effected in conventional distillation columns, in which case the temperature and pressure conditions to be employed can be determined by routine tests. Subsequently, the removed 2-methylbutanal-enriched stream and the removed stream enriched with the mixture of the isomeric α,β-unsaturated decenals can be converted to conversion products.

For example, the double bond in the α,β position relative to the carbonyl carbon atom is selectively hydrogenated with retention of the aldehyde group, which leads to a mixture of saturated isomeric decanals. The selective hydrogenation is conducted in a known manner over supported or unsupported catalysts containing, as hydrogenation active component, palladium, platinum, rhodium and/or nickel. Preference is given to working with palladium catalysts at temperatures of 120 to 180° C., preferably 140 to 160° C., and at a pressure of 1.5 to 5 MPa, preferably at 2 to 3 MPa. The hydrogenation output obtained is subsequently purified by distillation to free it of low and high boilers.

In one configuration of the process of the invention, the crude aldolization mixture of isomeric α,β-unsaturated decenals and unconverted pentanals itself can be subjected to the selective hydrogenation under the aforementioned conditions to obtain a mixture of saturated isomeric decanals and the unreacted pentanals. The subsequent distillative workup gives a volatile secondary stream in which 2-methylbutanal is enriched, and, separately therefrom, a stream enriched with a mixture of isomeric decanals.

The present invention therefore likewise relates to a process for preparing 2-methylbutanal from the secondary streams obtained in the preparation of mixtures of isomeric decanals, characterized in that a) a mixture comprising linear butenes is reacted in the presence of transition metal compounds of group VIII of the Periodic Table of the Elements with carbon monoxide and hydrogen at elevated temperature and elevated pressure to give a pentanal mixture;

b) the pentanal mixture obtained in step a) is converted in the presence of basic compounds to a mixture of isomeric α,β-unsaturated decenals;

c) the mixture obtained in step b) is selectively hydrogenated in the presence of a hydrogenation catalyst with hydrogen at elevated temperature and elevated pressure to give a mixture of isomeric decanals; and d) the mixture obtained in step c) is separated into a stream enriched with unconverted 2-methylbutanal and a stream enriched with a mixture of isomeric decanals;

with the proviso that the stream which has been separated off in step d) and is enriched with unconverted 2-methylbutanal is reacted with formaldehyde.

The unconverted 2-methylbutanal-enriched streams obtained by separation, appropriately by conventional distillation, of the crude aldolization product, or those obtained after selective hydrogenation and separation of the crude hydrogenation mixture, can be worked up by various variants and converted to various conversion products.

The unconverted 2-methylbutanal-enriched streams obtained contain, as by-product, unconverted residual contents of n-pentanal and possibly 3-methylbutanal, according to the isobutene content in the butene feed mixture. The exact composition of the unconverted 2-methylbutanal-enriched stream depends on the composition of the butene feed mixture and the aldolization conditions.

Typically, 2-methylbutanal, which has a boiling point of 92° C. at standard pressure, is freed of low boilers and high boilers in the unconverted 2-methylbutanal-enriched product stream by a further distillation. Fractions of n-pentanal having a boiling point of 103° C. at standard pressure can be removed here by conventional distillation methods in a further column having 10 to 100 trays as a product of high purity. If, however, residual amounts of 3-methylbutanal are present in the 2-methylbutanal-enriched stream, the boiling point difference from 3-methylbutanal having a boiling point of 92.5° C. at standard pressure is inadequate for sufficient separation with acceptable distillation complexity. In this case, 2-methylbutanal is removed together with 3-methylbutanal. If the particular field of use permits residual amounts of 3-methylbutanal in the 2-methylbutanal, the 2-methylbutanal can be converted to conversion products in this quality.

If, however, 2-methylbutanal and conversion products to be prepared therefrom are being demanded in virtually 3-methylbutanal-free quality with a residual 3-methylbutanal content of less than 0.2% by weight, based on the organic content, the 2-methylbutanal-enriched stream optionally containing 3-methylbutanal, either after prior distillative removal of n-pentanal or together with residual n-pentanal contents, is reacted, according to the invention, with formaldehyde in the presence of an aldolization catalyst. The treatment of α-alkyl-substituted aldehydes with formaldehyde to remove residual amounts of aldehydes having two hydrogen atoms on the α-carbon atom relative to the carbonyl group in the course of workup is also referred to as the methylenation reaction and is known per se from the prior art and is described, for example, in DE 3842186 A1 and DE 3744212 A1. The mixture comprising 2-methyl-/3-methylbutanal and optionally n-pentanal is treated with formaldehyde in the presence of an aldolization catalyst, typically with a mixture of a secondary amine, for example an amine of the general formula $R^1$—NH—$R^2$ where $R^1$ and $R^2$ are the same or different and are each alkyl radicals having 1 to 12 and preferably 3 to 5 carbon atoms, and a monocarboxylic acid having 1 to 10 carbon atoms or a di- or polycarboxylic acid having 2 to 10 carbon atoms. Preference is given to using, as aldolization catalyst, a mixture of di-n-butylamine and n-butyric acid. Alternatively, other aldolization catalysts are not ruled out. Formaldehyde is appropriately used as an aqueous solution in commercial concentration, for example in a concentration of 30%-50% by weight, in which case the molar ratio of formaldehyde to the sum total of aldehydes having two hydrogen atoms on the α-carbon atom relative to the carbonyl group is 1 to 2. The reaction is typically conducted at temperatures of 0 to 100° C. under autogenous pressure or slightly elevated pressure. Suitable reactors are the aggregates customary in chemical engineering, such as stirred tanks, stirred tank cascades, mixing pumps or flow tubes which may contain static mixers to intensify the mixing. In a particular process variant, the mixture comprising 2-methylbutanal, 3-methylbutanal and n-pentanal is distilled in the presence of formaldehyde and the aldolization catalyst, with distillative removal of virtually 3-methylbutanal-free and optionally n-pentanal-free 2-methylbutanal as the main fraction. As well as the organic phase, water is obtained as a result of the introduction of water and as a result of the formation of isopropylacrolein and possibly n-propylacrolein.

The methylenation at first forms, from formaldehyde and the secondary amine in an acidic medium, a Mannich salt which is dehydrated selectively with 3-methylbutanal and n-pentanal via the formation of the α-methylol derivative to isopropyl-acrolein and n-propylacrolein, while 2-methylbutanal remains unchanged. Isopropylacrolein has a boiling point of 108.5° C. at standard pressure and n-propylacrolein boils at 117° C. under standard pressure, and the two methylenation products can be separated by distillation from the 2-methylbutanal. The 3-methylbutanal content in the 2-methylbutanal removed is generally below 0.2% by weight, based on the organic component. This may optionally be followed by another fine distillation of the 2-methylbutanal.

The 2-methylbutanal obtained, having been purified via the methylenation reaction with subsequent distillation, can be used as such, for example for production of fragrances.

2-Methylbutanal can likewise be oxidized by methods known per se (Ullmann's Encyclopedia of Industrial Chemistry, 6th edition, 2003, Wiley-VCH Verlag GmbH & Co. KGaA, Weinheim, vol. 6, pages 497-502) to 2-methylbutyric acid. The oxidation is preferably effected in the liquid phase, for example in tubular reactors provided with a distributor tray. Suitable oxidizing agents are oxygen or oxygen-containing gases. Operation is effected at temperatures of 20 to 100° C., preferably 20 to 80° C., and typically at standard pressure, although process settings up to a pressure (absolute) of 0.8 MPa are not ruled out.

It is advisable to conduct the conversion in the presence of alkali metal or alkaline earth metal salts of weak acids. Especially in the case of oxidation of α-branched aldehydes in which the carbon atom adjacent to the carbonyl carbon atom bears the branch, the prior art suggests the presence of small amounts of alkali metal carboxylates to improve selectivity (DE 950 007, DE 100 10 771 C1). Appropriately, the oxidation is conducted in the presence of 1 to 30 mmol, preferably 1 to 15 mmol and especially 1 to 8 mmol per mole of aldehyde, calculated as alkali metal or alkaline earth metal. Preference is given to working in the presence of potassium or sodium.

It is also possible to use a combination of alkali metal or alkaline earth metal carboxylates with transition metal compounds as discussed in EP 1 854 778 A1.

If an isobutene-free butene feed mixture is used for the hydroformylation step, the unconverted 2-methylbutanal-enriched stream obtained is 3-methylbutanal-free, but may contain residual amounts of n-pentanal, which is dehydrated via the methylenation reaction to give n-propylacrolein. In that case, the oxidation, as described above, affords 2-methylbutyric acid.

2-Methylbutanal can likewise be converted via reductive amination to 2-methylbutylamines. This involves reacting the 2-methylbutanal with ammonia or a primary or secondary amine with hydrogen in the presence of a standard amination catalyst, forming primary, secondary and tertiary 2-methylbutylamines. The degree of amination is determined by the excess of ammonia or of the second amine, such as n-butylamine or 2-ethylhexylamine, a high excess of ammonia promoting the formation of the primary 2-methylbutylamine.

The reductive amination is conducted in reactors customary in the art, for example in stirred reactors over fixed bed amination catalysts at temperatures in the range from 100 to 200° C., preferably from 110 to 150° C., and at pressures in the range from 0.1 to 40 MPa, preferably of 0.5 to 30 MPa. Preferably, the conversion is effected over supported or unsupported nickel or cobalt catalysts which may additionally contain promoters such as oxides of calcium, barium, zinc, aluminum, zirconium and chromium. The use of such amination catalysts is discussed, for example, in DE 10 2012 014 395 B3.

2-Methylbutanal can likewise be hydrogenated to 2-methylbutanol. The hydrogenation is effected in the presence of standard hydrogenation catalysts by gas phase or liquid phase methods known per se (Ullmann's Encyclopedia of Industrial Chemistry, 6th edition, 2003, Wiley-VCH Verlag GmbH & Co. KGaA, Weinheim, vol. 2, page 24; vol. 25, pages 286-289). Suitable examples of hydrogenation catalysts are nickel or copper catalysts, preferably nickel catalysts. The hydrogenation is effected generally at hydrogen pressures of 1 to 10 MPa and at temperatures of 100 to 180° C. in the gas phase, in the liquid phase or any combination thereof. In a suitable process regime, in a first hydrogenation stage, hydrogenation is effected over the copper catalyst in the gas phase, and subsequently in a second hydrogenation stage over the nickel catalyst in the liquid phase. For purification, the 2-methylbutanol obtained is distilled. 2-Methylbutanol can likewise be converted by catalytic methods known per se by ammonolysis with ammonia or primary or secondary amines to 2-methylbutylamines.

The mixtures of isomeric decanals obtained by the process of the invention can subsequently be oxidized to a mixture of isomeric decanoic acids. This method is known per se and is discussed, for example, in DE 101 08 474 A1, DE 101 08 475 A1, DE 102 25 282 A1 and DE 10 2009 027 978 A1. The oxidation of the decanal mixture is effected in accordance with the aforementioned conditions for the oxidation of 2-methylbutanal, preferably in the presence of alkali metal or alkaline earth metal compounds. Low and high boilers are removed from the crude acid mixture obtained after the oxidation by means of distillation under standard conditions. The distillation residue which comprises the alkali metal or alkaline earth metal 2-propylheptanoates, with or without transition metals, is removed and can be fed back to the aldehyde feed, optionally after addition of fresh alkali metal or alkaline earth metal 2-propylheptanoates or alkali metal or alkaline earth metal compounds which are converted to the 2-propylheptanoates under the reaction conditions, and optionally of fresh transition metal compounds.

The mixture of isomeric decanoic acids obtained contains, according to the composition of the butene feed mixture, the reaction conditions and the separation sharpness chosen in the distillative workups, varying proportions of 2-propylheptanoic acid, 2-propyl-4-methylhexanoic acid and further decanoic acids which can be derived from the α,β-unsaturated decenals. For example, one decanoic acid mixture contains more than 90 mol % of 2-propylheptanoic acid and less than 5 mol % of 2-propyl-4-methylhexanoic acid, based on the sum total of decanoic acids, and can be used, for example, by processes known per se for preparation of derivatives such as the vinyl esters, carboxylic esters, acid anhydrides, acid halides or acid amides.

The decanal mixture obtained after the selective hydrogenation can likewise be converted via reductive amination to a mixture of isomeric decylamines, which is effected analogously to the reductive amination of 2-methylbutanal. The mixture of decylamines obtained is particularly suitable for use as an anticorrosive in lubricants, as an auxiliary in rubber formulations, as a vulcanization accelerator and as an additive in lubricants, for example in the form of the dithio-carbamates thereof, or corresponding salts such as molybdenum, zinc or sodium dithiocarbamates.

The mixture of isomeric α,β-unsaturated decenals obtained via the aldolization reaction can also be hydrogenated completely to give a mixture of isomeric decanols. It is likewise possible to hydrogenate the decanal mixture to give a mixture of isomeric decanols. The hydrogenation is effected analogously to the conditions for hydrogenation of 2-methylbutanal and is known per se and is discussed, for example, in EP 0 366 089 A2, DE 42 100 26 A1 and DE 43 33 324 A1.

For purification, the mixture of isomeric decanols obtained is distilled. According to the composition of the butene feed mixture, the reaction conditions and the separation sharpness chosen in the distillative workup, it contains varying proportions of 2-propylheptanol, 2-propyl-4-methylhexanol and further decanols which can be derived from the isomeric $\alpha,\beta$-unsaturated decenals. The mixture of isomeric decanols obtained can be used as alcohol component for the preparation of esters of aromatic and aliphatic di- and polycarboxylic acids such as phthalic acid or phthalic anhydride, terephthalic acid, trimellitic acid or adipic acid. These esters have plasticizing properties with respect to thermoplastics, for example PVC, and these can be adjusted via the composition of the decanol mixture. In order to obtain particularly cold-flexible plastics moldings, the 2-propyl-heptanol content in the decanol mixture to be esterified should be at a maximum.

The mixture of isomeric decanols obtained can likewise be converted by catalytic methods known per se by ammonolysis with ammonia or primary or secondary amines to a mixture of isomeric decylamines.

The inventive preparation of 2-methylbutanal from secondary streams obtained in the production of mixtures of isomeric $\alpha,\beta$-unsaturated decenals, and the conversion products of 2-methylbutanal and the mixtures of isomeric $\alpha,\beta$-unsaturated decenals, allows the butene feed mixture to be utilized in a particularly advantageous and economically viable manner.

The invention claimed is:

1. A process for preparing 2-methylbutanal from the secondary streams obtained in the preparation of mixtures of isomeric $\alpha,\beta$-unsaturated decenals, characterized in that
   a) a mixture comprising linear butenes is reacted in the presence of transition metal compounds of group VIII of the Periodic Table of the Elements with carbon monoxide and hydrogen at elevated temperature and elevated pressure to give a pentanal mixture;
   b) the pentanal mixture obtained in step a) is converted in the presence of basic compounds to a mixture of isomeric $\alpha,\beta$-unsaturated decenals; and
   c) the mixture obtained in step b) is separated into a stream enriched with unconverted 2-methylbutanal and a stream enriched with a mixture of isomeric $\alpha,\beta$-unsaturated decenals; with the proviso that the stream which has been separated off in step c) and is enriched with unconverted 2-methylbutanal is reacted with formaldehyde.

2. The process as claimed in claim 1, characterized in that the reaction with formaldehyde is effected in the presence of a secondary amine and a mono-, di- or polycarboxylic acid.

3. The process as claimed in claim 2, characterized in that distillation is effected in the course of the reaction with formaldehyde.

4. The process as claimed in claim 1, characterized in that the 2-methylbutanal obtained in step c) is oxidized to 2-methylbutyric acid, hydrogenated to 2-methylbutanol or reductively aminated to 2-methylbutylamines.

5. The process as claimed in claim 1, characterized in that the mixture of isomeric $\alpha,\beta$-unsaturated decenals obtained in step c) is completely hydrogenated to give a mixture of isomeric decanols or selectively hydrogenated to give a mixture of isomeric decanals.

6. The process as claimed in claim 5, characterized in that the mixture of isomeric decanals is oxidized to give a mixture of isomeric decanoic acids or reductively aminated to give a mixture of isomeric decylamines.

7. A process for preparing 2-methylbutanal from the secondary streams obtained in the preparation of mixtures of isomeric decanals, characterized in that
   a) a mixture comprising linear butenes is reacted in the presence of transition metal compounds of group VIII of the Periodic Table of the Elements with carbon monoxide and hydrogen at elevated temperature and elevated pressure to give a pentanal mixture;
   b) the pentanal mixture obtained in step a) is converted in the presence of basic compounds to a mixture of isomeric $\alpha,\beta$-unsaturated decenals;
   c) the mixture obtained in step b) is selectively hydrogenated in the presence of a hydrogenation catalyst with hydrogen at elevated temperature and elevated pressure to give a mixture of isomeric decanals; and
   d) the mixture obtained in step c) is separated into a stream enriched with unconverted 2-methylbutanal and a stream enriched with a mixture of isomeric decanals; with the proviso that the stream which has been separated off in step d) and is enriched with unconverted 2-methylbutanal is reacted with formaldehyde.

8. The process as claimed in claim 7, characterized in that the reaction with formaldehyde is effected in the presence of a secondary amine and a mono-, di- or polycarboxylic acid.

9. The process as claimed in claim 8, characterized in that distillation is effected in the course of the reaction with formaldehyde.

10. The process as claimed in claim 7, characterized in that the 2-methylbutanal obtained in step d) is oxidized to 2-methylbutyric acid, hydrogenated to 2-methylbutanol or reductively aminated to 2-methylbutylamines.

11. The process as claimed in claim 1, characterized in that the reaction with formaldehyde is followed by distillative removal of 2-methylbutanal.

12. The process as claimed in claim 11, characterized in that the 2-methylbutanal obtained is oxidized to 2-methylbutyric acid, hydrogenated to 2-methylbutanal or reductively aminated to 2-methylbutylamines.

13. The process as claimed in claim 7, characterized in that the mixture of isomeric decanals obtained in step d) is hydrogenated to give a mixture of isomeric decanols, oxidized to give a mixture of isomeric decanoic acids or reductively aminated to give a mixture of isomeric decylamines.

14. The process as claimed in claim 2, characterized in that the 2-methylbutanal obtained in step c) is oxidized to 2-methylbutyric acid, hydrogenated to 2-methylbutanol or reductively aminated to 2-methylbutylamines.

15. The process as claimed in claim 3, characterized in that the 2-methylbutanal obtained in step c) is oxidized to 2-methylbutyric acid, hydrogenated to 2-methylbutanol or reductively aminated to 2-methylbutylamines.

16. The process as claimed in claim 2, characterized in that the mixture of isomeric $\alpha,\beta$-unsaturated decenals obtained in step c) is completely hydrogenated to give a mixture of isomeric decanols or selectively hydrogenated to give a mixture of isomeric decanals.

17. The process as claimed in claim 3, characterized in that the mixture of isomeric $\alpha,\beta$-unsaturated decenals obtained in step c) is completely hydrogenated to give a mixture of isomeric decanols or selectively hydrogenated to give a mixture of isomeric decanals.

18. The process as claimed in claim 8, characterized in that the 2-methylbutanal obtained in step d) is oxidized to 2-methylbutyric acid, hydrogenated to 2-methylbutanol or reductively aminated to 2-methylbutylamines.

19. The process as claimed in claim 9, characterized in that the 2-methylbutanal obtained in step d) is oxidized to 2-methylbutyric acid, hydrogenated to 2-methylbutanol or reductively aminated to 2-methylbutylamines.

20. The process as claimed in claim 7, characterized in that the reaction with formaldehyde is followed by distillative removal of 2-methylbutanal.

* * * * *